United States Patent [19]

Berg

[11] Patent Number: 5,407,542
[45] Date of Patent: Apr. 18, 1995

[54] SEPARATION OF 3-METHYL-2-BUTANOL FROM 1-BUTANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 305,436

[22] Filed: Sep. 13, 1994

[51] Int. Cl.⁶ .......................... B01D 3/36; C07C 29/82
[52] U.S. Cl. ........................................ 203/58; 203/59; 203/60; 203/63; 568/913
[58] Field of Search ....................... 203/63, 59, 60, 58; 568/913

[56] References Cited

U.S. PATENT DOCUMENTS

| | | | |
|---|---|---|---|
| 2,483,246 | 9/1949 | Stribley | 203/60 |
| 2,500,329 | 3/1950 | Steitz | 203/69 |
| 5,338,410 | 8/1994 | Berg | 203/60 |

*Primary Examiner*—Wilbur Bascomb, Jr.

[57] ABSTRACT

3-Methyl-2-butanol is difficult to separate from 1-butanol by conventional distillation or rectification because of the proximity of their boiling points. 3-Methyl-2-butanol can be readily separated from 1-butanol by azeotropic distillation. Effective agents are methyl acetoacetate and dioxane.

1 Claim, No Drawings

SEPARATION OF 3-METHYL-2-BUTANOL FROM 1-BUTANOL BY AZEOTROPIC DISTILLATION

FIELD OF THE INVENTION

This invention relates to a method for separating 3-methyl-2-butanol from 1-butanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of alcohols, e.g. the Fischer-Tropsch process which produces a series of homologous alcohols. Two of the alcohols often present are 3-methyl-2-butanol, B.P.=112° C. and 1-butanol, B.P.=118° C. The relative volatility between these two is 1.22 which makes it very difficult to separate them by conventional rectification. Azeotropic distillation would be an attractive method of effecting the separation of 3-methyl-2-butanol from 1-butanol if agents can be found that (1) will create a large apparent relative volatility between 3-methyl-2-butanol and 1-butanol and (2) are easy to recover from 3-methyl-2-butanol. Table 2 shows the relative volatility required to obtain 99% purity. With no agent, the relative volatility is 1.22 and 61 actual plates are required. With an agent giving a relative volatility of 1.9, only 20 plates are required.

TABLE 2

Theoretical And Actual Plates Required vs. Relative Volatility For 3-Methyl-2-butanol - 1-Butanol Separation

| Relative Volatility | Theoretical Plates Required At Total Reflux, 99% Purity | Actual Plates Required 75% Efficiency |
|---|---|---|
| 1.22 | 46 | 61 |
| 1.4 | 27 | 36 |
| 1.9 | 15 | 20 |

OBJECTIVE OF THE INVENTION

The object of this invention is to provide a process or method of azeotropic distillation that will enhance the relative volatility of 3-methyl-2-butanol from 1-butanol in their separation in a rectification column. It is a further object of this invention to identify organic compounds which in addition to the above constraints, are stable, can be separated from 3-methyl-2-butanol and recycled to the azeotrope column with little decomposition.

SUMMARY OF THE INVENTION

The objects of this invention are provided by a process for separating 3-methyl-2-butanol from 1-butanol which entails the use of certain organic compounds as the agent in azeotropic distillation.

DETAILED DESCRIPTION OF THE INVENTION

I have discovered that certain organic compounds will greatly improve the relative volatility of 3-methyl-2-butanol to 1-butanol and permit the separation of 3-methyl-2-butanol by rectification when employed as the agent in azeotropic distillation. Table 3 lists the compounds that I have found to be effective. They are methyl acetoacetate, dimethoxymethane, 2,2-dimethoxypropane, 1-methoxy-2-propanol, dioxane and n-butyl amine.

TABLE 3

Effective Azeotropic Distillation Agents For Separating 3-Methyl-2-butanol From 1-Butanol

| Compounds | Relative Volatility |
|---|---|
| None | 1.22 |
| Methyl acetoacetate | 1.4 |
| Dimethoxymethane | 1.35 |
| 2,2-Dimethoxypropane | 1.3 |
| 1-Methoxy-2-propanol | 1.3 |
| Dioxane | 1.9* |
| n-Butyl amine | 1.4 |

*Data Obtained In Multiplate Column

THE USEFULNESS OF THE INVENTION

The usefulness or utility of this invention can be demonstrated by referring to the data presented in Tables 2 and 3. All of the succcessful agents show that 3-methyl-2-butanol can be separated from 1-butanol by means of azeotropic distillation in a rectification column and that the ease of separation as measured by relative volatility is considerable.

WORKING EXAMPLES

Example 1

Thirteen grams of 3-methyl-2-butanol, 27 grams of 1-butanol and 40 grams of methyl acetoacetate were charged to a vapor-liquid equilibrium still and refluxed for four hours. Analysis indicated a vapor composition of 22.1% 3-methyl-2-butanol, 77.9% 1-butanol; a liquid composition of 16.8% 3-methyl-2-butanol, 83.2% 1-butanol. This is a relative volatility of 1.4.

Example 2

Thirty grams of 3-methyl-2-butanol, 70 grams of 1-butanol and 150 grams of dioxane were placed in the stillpot of a 5.6 theoretical plate glass perforated plate rectification column and refluxed for five hours. The overhead composition was 97.9% 3-methyl-2-butanol, 2.1% 1-butanol; the bottoms composition was 56.5% 3-methyl-2-butanol, 43.5% 1-butanol. This is a relative volatility of 1.9.

I claim:

1. A method for recovering 3-methyl-2-butanol from a mixture of 3-methyl-2-butanol and 1-butanol which comprises distilling a mixture of 3-methyl-2-butanol and 1-butanol in the presence of an azeotrope forming agent, recovering the 3-methyl-2-butanol and the azeotrope forming agent as everhead product and obtaining the 1-butanol as bottoms product, wherein said azeotrope forming agent consists of one material selected from the group consisting of methyl acetoacetate, dimethoxymethane, 2,2-dimethoxypropane, dioxane, 1-methoxy-2-propanol and n-butyl amine.

* * * * *